United States Patent [19]

Suganuma et al.

[11] 4,279,888

[45] Jul. 21, 1981

[54] ORAL COMPOSITION

[75] Inventors: Nobuo Suganuma, Funabashi; Michio Uematsu, Isehara; Hiroshi Mandai, Chiba; Yasunobu Horiguchi, Kamagaya; Koji Masamizu, Tokyo, all of Japan

[73] Assignee: Lion Corporation, Tokyo, Japan

[21] Appl. No.: 107,868

[22] Filed: Dec. 28, 1979

[30] Foreign Application Priority Data

Dec. 29, 1978 [JP] Japan .............................. 53-165284
Dec. 30, 1978 [JP] Japan .............................. 53-165049

[51] Int. Cl.$^3$ .................... A61K 7/16; A61K 7/18; A61K 7/28
[52] U.S. Cl. ....................................... 424/49; 424/50; 424/52; 424/57
[58] Field of Search ................................... 424/49-58

[56] References Cited

PUBLICATIONS

Chem. Abstracts 81 #120937e (1974), 82 #140440m (1975), 83 #178353u (1975), 83 #149344m (1975), 86 #157374y (1977), 90 #174523w (1979), 1967-1979, D-Glucitol, 4-O-A-D-Glucopyranosyl-B-fatty acid esters.

*Primary Examiner*—Shep K. Rose
*Attorney, Agent, or Firm*—Birch, Stewart, Kolasch & Birch

[57] ABSTRACT

An oral composition contains as a surface-active agent 0.1 to 5% by weight of a fatty acid ester of a sugar alcohol selected from the group consisting of lactitol, maltitol, maltotriitol, maltotetraitol, maltopentaitol, maltohexaitol, maltoheptaitol and mixtures thereof. The ester has an acyl group with 8 to 20 carbon atoms such as lauroyl. The oral composition which may be applicable as toothpaste, toothpowder, mouthwashes and the like has a pleasant taste as well as a good foaming power.

22 Claims, No Drawings

ORAL COMPOSITION

BACKGROUND OF THE INVENTION

This invention relates to oral compositions including toothpastes, toothpowders, mouthwashes and the like. More particularly, this invention relates to oral compositions which contain a fatty acid ester of a sugar alcohol such as lactitol and maltitol.

Oral compositions such as dentifrices generally contain surface-active agents for enhancing the detergency thereof. Such agents for oral application are required to foam well and be free of uncomfortable factors such as bitter and rough tastes and nasty odor as well as being safe. In addition, it is essential that dentifrices containing a surface-active agent can be stored for a prolonged period of time without any deterioration including discoloration and syneresis since dentifrices may be displayed in the store for a relatively long period of time before they are used by the consumers.

Surface-active agents used for oral compositions are anionic and nonionic. In general, anionic surface-active agents are widely used because of their good foaming power. It is recognized that nonionic surface-active agents are superior to anionic agents in stabilization of effective ingredients and juice effect. For example, sucrose fatty acid esters which have recently come to prevail are recognized as having improved juice effect. However, many of conventional nonionic surface-active agents have a poor foaming power and give uncomfortable taste and odor. Sucrose laurate and sucrose myristate, for example, taste bitter though they have a relatively good foaming power among various sucrose fatty acid esters. Furthermore, when dentifrices containing sucrose fatty acid esters are stored for an extended period of time or at a relatively high temperature (as occurring during ordinary storage in summer), they tend to be discolored yellow and are susceptible to syneresis, resulting in unacceptable dentifrices.

SUMMARY OF THE INVENTION

Therefore, an object of this invention is to provide an oral composition which can give a favorable feeling (taste, odor and foaming ability) upon use.

Another object of this invention is to provide an oral composition having improved storage stability.

According to this invention, there is provided an oral composition which comprises a fatty acid ester of a sugar alcohol selected from the group consisting of lactitol, maltitol, maltotriitol, maltotetraitol, maltopentaitol, maltohexaitol, maltoheptaitol, and mixtures thereof.

The use of the above-mentioned sugar alcohol fatty acid esters results in an oral composition which is free of bitter, rough and other unfavorable tastes or has a pleasant taste as compared with those containing sucrose fatty acid esters. The oral composition according to this invention is also good in juice effect and stable for a prolonged period of storage. The present oral compositions in the form of dentifrices, for example, are less susceptible to deterioration including discoloration and syneresis upon prolonged storage. Since the above-mentioned sugar alcohols are more resistant to heat, acid and alkali and less readily fermented than sucrose, their fatty acid esters are more suitable for oral application. In addition, the esters according to this invention allow ionic effective ingredients such as bactericides, enzymes, fluorine compounds and the like to be blended in a stable manner and to display their full function upon use.

The above and other objects, features and advantages of this invention will become more apparent and understandable from the following detailed description and examples.

DETAILED DESCRIPTION OF THE INVENTION

The feature of this invention is that an oral composition contains a fatty acid ester of a sugar alcohol selected from the group consisting of lactitol, maltitol, maltotriitol, maltotetraitol, maltopentaitol, maltohexaitol, maltoheptaitol and mixtures thereof. It may take the form of toothpastes, toothpowders, mouthwashes or the like.

The sugar alcohol fatty acid esters may be prepared from the corresponding sugar alcohol and fatty acid or fatty acid derivative.

Lactitol may be prepared by reducing lactose as by any known methods, for example, electrolytic reduction or high-pressure catalytic hydrogenation or using a metal hydride. Maltitol, maltotriitol, maltotetraitol, maltopentaitol, maltohexaitol and maltoheptaitol may be prepared similarly from maltose, maltotriose, maltotetraose, maltopentaose, maltohexaose and maltoheptaose, respectively, which are in turn, prepared by hydrolysis of starch, specifically, amylose. Adjustment of the degree of hydrolysis in the preparation of the saccharides may result in mixtures containing a major amount of maltose, maltotriose or maltoheptaose, which may be directly reduced by any of the above-mentioned methods. The resulting sugar alcohol mixtures may be used in the subsequent esterification or may be fractionated into separate components when a single sugar alcohol is desired. The saccharide mixtures obtained after the hydrolysis may be separated into each component which is then reduced into the corresponding sugar alcohol. Thus obtained sugar alcohol or sugar alcohols may be reacted with a fatty acid or fatty acid derivative to be described hereinafter to give a sugar alcohol fatty acid ester or a mixture thereof, which may be blended into an oral composition.

The above-mentioned sugar alcohols have higher heat, alkali and acid resistances and are less susceptible to fermentation than sucrose.

The fatty acid or fatty acid derivative which is another component of the ester may have a linear or branched acyl group, and the acyl group may preferably have 8 to 20 carbon atoms from a viewpoint of foaming ability and taste. Most preferred are saturated acyl groups having 10 to 18 carbon atoms and unsaturated acyl groups having 16 to 18 carbon atoms. Examples of the acyl groups are capryl, lauroyl, tridecanoyl, 2-methyllauroyl, myristoyl, pentadecanoyl, palmitoyl, stearoyl, isostearoyl, oleoyl, etc. The acyl group may be incorporated into the ester alone or in admixture. Examples of admixed acyl groups in an ester are coconut oil fatty acid residues, palm oil fatty acid residues, tallow fatty acid residues, coconut oil-hardened tallow mixed fatty acid residues, etc.

In this invention, the fatty acid esters of the sugar alcohol which contains at least 50% by weight of maltitol are preferably used as well as lactitol fatty acid esters.

The sugar alcohol fatty acid esters according to this invention preferably have an average degree of esterification of 0.2 to 1.5, more preferably 0.3 to 1.0 per glucose unit, galactose unit or reduced glucose unit. Particularly, the ester mixture to be blended in the oral composition preferably contains 60% by weight or more of the ester having an average degree of esterification of 0.5 per the unit. Illustratively, the fatty acid esters of the sugar alcohol which contains at least 50% by weight of maltitol and lactitol fatty acid esters may preferably have an average degree of esterification of 0.5 to 3.0, especially 0.8 to 2.0, and a monoester content of at least 60% by weight.

It is to be noted that the average degree of esterification per unit of 0.3 corresponds to, for example, a degree of esterification of 0.6 for a theoretical lactitol ester or an average degree of esterification of 0.6 for an actual mixture of unreacted lactitol, lactitol monoacyl ester and lactitol diacyl ester.

Generally, the sugar alcohol fatty acid ester may be blended in the oral composition in an amount of 0.1 to 5% by weight, preferably 0.3 to 3% by weight of the total amount of the oral composition.

The oral composition according to this invention may contain one or more of the sugar alcohol fatty acid esters, optionally in admixture with another surface-active agent. The additional surface-active agents used herein include anionic surface-active agents such as alkyl sulfates, olefin sulfonates, monoglyceride sulfates and soaps; nonionic surface-active agents such as fatty acid monoglycerides, fatty acid alkylol amides, polyoxyethylene sorbitan fatty acid esters, sorbitan fatty acid esters; amphoteric surface-active agents, and mixtures thereof.

The oral composition according to this invention may comprise any known ingredients depending on the type desired therefor. The oral composition in the form of dentifrices may comprise a polishing agent such as dicalcium phosphate dihydrate or anhydride, calcium carbonate, calcium pyrophosphate, insoluble sodium metaphosphate, silicic acid anhydride and hydrate, aluminosilicate, alumina, aluminum hydroxide, resins and the like generally in an amount of 5–95 wt%, preferably in an amount of 10–50 wt% for toothpastes; a humectant such as glycerine, sorbit, propylene glycol, polyethylene glycol, and the like generally in an amount of 0–70 wt%, preferably 10–60 wt% for toothpastes; a binder such as carboxymethyl cellulose, carrageenan, sodium alginate, veegum, hydroxyethyl cellulose, polyvinyl alcohol and the like generally in an amount of 0 to 5 wt%, preferably in an amount of 0.5 to 3 wt% for toothpastes; a sweetener such as sodium saccharin, ammonium glycyrrhetinate, stevioside, neohesperidin dihydrochalcone, p-methoxycinnamic aldehyde, perillartine and the like in an amount of 0 to 2 wt%, preferably 0.1 to 1 wt%; and a flavor such as menthol, carvone, anethole and the like generally in an amount of 0.1 to 7 wt%, preferably 0.5 to 2 wt%. Also included are a fluorine compund such as sodium monofluorophosphate, tin fluoride, sodium fluoride and the like, a bactericide such as hydrogen chlorohexidine hydrochloride and the like; an inorganic phosphate such as disodium hydrogen phosphate; an organic phosphate such as glycerophosphate; an enzyme such as dextranase, amylase and the like; an effective ingredient for antiinflammatory such as ε-aminocaproic acid, tranexamic acid, allantoinates and the like; and other effective ingredients such as sodium choride. Toothpastes may be prepared in a conventional manner from the above ingredients by kneading the desired ingredients with water.

Oral cleaning agents such as mouthwashes may also be prepared by dissolving the desired ingredients in a solvent so as to meet the desired form of the final product.

The oral composition according to this invention may generally have a pH of 5.5 to 10, preferably 6 to 8.5.

The invention will be more readily understood with reference to the following Examples. However, it is to be understood that the invention is not limited to the Examples. All parts and percents are by weight.

EXAMPLE 1

The ingredients listed in Table I were kneaded with water to prepare a toothpaste containing lactitol monolaurate as a foaming agent (Example 1) and a toothpaste containing sucrose monolaurate (Comparative Example 1). Both the toothpastes were tested for feelings including taste and foaming ability by a pair comparison procedure using a nine-membered panel. A stability test was carried out by storing the toothpastes at 50° C. for one month. The results are shown in Tables II and III.

The lactitol monolaurate and sucrose monolaurate used both have an average degree of esterification of about 1.2 and a monoester content of about 80%.

TABLE I

| Ingredient | Example 1 | Comparative Example 1 |
|---|---|---|
| Dicalcium phosphate | 50.0 | 50.0 |
| Sorbit | 20.0 | 20.0 |
| Carboxymethyl cellulose | 1.0 | 1.0 |
| Sodium saccharin | 0.1 | 0.1 |
| Sucrose monolaurate | — | 2.0 |
| Lactitol monolaurate | 2.0 | — |
| Flavor | 1.0 | 1.0 |
| Water | balance | balance |
| Total | 100.0% | 100.0% |

TABLE II

| | Feeling | |
|---|---|---|
| | Taste | Foaming |
| Number of persons recommending Example 1 | 8 | 2 |
| Number of persons recommending Comparative Example 1 | 1 | 2 |
| Number of persons answering both are equal | 0 | 5 |

TABLE III

| | Stability (50° C., 1 month) | | | |
|---|---|---|---|---|
| | Extrudability | Syneresis | Surface smoothness | Discoloration |
| Example 1 | good | none | good | none |
| Comparative Example 1 | good | slight | slightly rough | discolored |

"Extrudability" means the easiness with which a toothpaste is extruded on a brush; "syneresis" means the extent of separation of liquid phase from a toothpaste, "surface smoothness" means the smoothness of the surface of a toothpaste extruded on a brush, and "discoloration" means a difference in color of a toothpaste before and after the 1 month storage.

As apparent from Table II, the toothpaste of Example 1 is improved in taste over the comparative toothpaste without impairing foaming ability.

Table III reveals that the toothpaste of Example 1 is improved in syneresis, surface smoothness and discoloration.

Similar results were obtained by substituting coconut oil fatty acid esters, hardened tallow fatty acid esters and oleic acid esters of lactitol and sucrose for the lactitol monolaurate and sucrose monolaurate, respectively.

EXAMPLE 2

The ingredients listed in Table IV were kneaded with water to prepare a toothpaste containing maltitol monolaurate having an average degree of polymerization $\overline{N}$ of 1 as a foaming agent (Example 2) and a toothpaste containing sucrose monolaurate (Comparative Example 2). A feeling test (taste) and a stability test (storage at 50° C. for 1 month) were carried out in the same manner as in Example 1. The results are shown in Tables V and VI.

It is to be noted that the average degree of polymerization $\overline{N}$ is an average number of glucose units excluding reduced glucose units. The maltitol monolaurate and sucrose monolaurate used both have an average degree of esterification of about 1.2 and a monoester content of about 80%.

TABLE IV

| Ingredient | Example 2 | Comparative Example 2 |
|---|---|---|
| Dicalcium phosphate | 50.0 | 50.0 |
| Sorbit | 20.0 | 20.0 |
| Carboxymethyl cellulose | 1.0 | 1.0 |
| Sodium saccharin | 0.1 | 0.1 |
| Sucrose monolaurate | — | 2.0 |
| Maltitol monolaurate | 2.0 | — |
| Flavor | 1.0 | 1.0 |
| Water | balance | balance |
| Total | 100.0% | 100.0% |

TABLE V

| | Feeling |
|---|---|
| | Taste |
| Number of persons recommending Example 2 | 9 |
| Number of persons recommending Comparative Example 2 | 0 |
| Number of persons answering both are equal | 0 |

TABLE VI

| | Stability (50° C., 1 month) | | | |
|---|---|---|---|---|
| | Extrudability | Syneresis | Surface smoothness | Discoloration |
| Example 2 | good | none | good | none |
| Comparative Example 2 | good | slight | slightly rough | Discolored |

As seen from Tables V and VI, the toothpaste of the Example 2 is improved in taste, syneresis, surface smoothness and discoloration. Similar results were obtained by substituting coconut oil fatty acid esters, hardened tallow fatty acid esters and oleic acid esters of maltitol and sucrose for the maltitol monolaurate and sucrose monolaurate, respectively.

EXAMPLE 3

Toothpaste

| Ingredient | % by weight |
|---|---|
| Dicalcium phosphate | 50.0 |
| Sorbit | 20.0 |
| Lactitol monolaurate* | 2.0 |
| Carboxymethyl cellulose | 1.0 |
| Sodium saccharin | 0.1 |
| Flavor | 1.0 |
| Water | balance |
| Total : | 100.0 |

*Degree of esterification = 1.1
Monoester content = 90%

EXAMPLE 4

Toothpaste

| Ingredient | % by weight |
|---|---|
| Dicalcium phosphate | 50.0 |
| Glycerin | 20.0 |
| Lactitol coconut oil fatty acid monoester* | 3.0 |
| Carrageenan | 1.0 |
| Sodium saccharin | 0.1 |
| Flavor | 1.0 |
| Water | balance |
| Total : | 100.0 |

*Degree of esterification = 1.4
Monoester content = 70%

EXAMPLE 5

Toothpaste

| Ingredient | % by weight |
|---|---|
| Dicalcium phosphate | 50.0 |
| Sorbit | 20.0 |
| Maltitol monolaurate* | 2.0 |
| Carboxymethyl cellulose | 1.0 |
| Sodium saccharin | 0.1 |
| Flavor | 1.0 |
| Water | balance |
| Total : | 100.0 |

*Average degree of polymerization ($\overline{N}$) = 1.1
Degree of esterification = 1.1
Monoester content = 90%

EXAMPLE 6

Toothpaste

| Ingredient | % by weight |
|---|---|
| Dicalcium phosphate | 50.0 |
| Glycerin | 20.0 |
| Maltitol coconut oil fatty acid monoester* | 3.0 |
| Carrageenan | 1.0 |
| Sodium saccharin | 0.1 |
| Flavor | 1.0 |
| Water | balance |
| Total : | 100.00 |

*$\overline{N}$ = 1.1
Degree of esterification = 1.4
Monoester content = 70%

The toothpastes of Examples 3–6 were prepared by kneading the ingredients in water.

EXAMPLE 7

Toothpowder

| Ingredient | % by weight |
| --- | --- |
| Calcium carbonate | 75.0 |
| Glycerin | 10.0 |
| Lactitol myristate* | 1.0 |
| Sodium lauryl sulfate | 0.5 |
| Sodium saccharin | 0.1 |
| Flavor | 1.0 |
| Water | balance |
| Total : | 100.0 |

*Degree of esterification = 1.8

EXAMPLE 8

Toothpowder

| Ingredient | % by weight |
| --- | --- |
| Calcium carbonate | 75.0 |
| Glycerin | 10.0 |
| Mixed sugar alcohol myristate* | 1.0 |
| Sodium lauryl sulfate | 0.5 |
| Sodium saccharin | 0.1 |
| Flavor | 1.0 |
| Water | balance |
| Total : | 100.0 |

*Esterified product of a mixture of 60% maltitol, 20% maltotriitol and 20% maltotetraitol, having a degree of esterification of 1.8.

The toothpowders of Examples 7 and 8 were prepared by thoroughly mixing the ingredients.

EXAMPLE 9

Liquid dentifrice

| Ingredient | % by weight |
| --- | --- |
| Glycerin | 35.0 |
| Hydroxyethyl cellulose | 5.0 |
| Lactitol monopalmitate* | 3.0 |
| Chlorohexidine hydrochloride | 0.01 |
| Dipotassium glycyrrhitinate | 0.1 |
| Stevioside | 0.1 |
| Ethylalcohol | 3.0 |
| Flavor | 1.0 |
| Water | balance |
| Total : | 100.0 |

*Degree of esterification = 1.05
Monoester content = 95%

EXAMPLE 10

Liquid dentifrice

| Ingredient | % by weight |
| --- | --- |
| Glycerin | 35.0 |
| Hydroxyethyl cellulose | 5.0 |
| Maltitol monopalmitate* | 3.0 |
| Chlorohexidine hydrochloride | 0.01 |
| Dipotassium glycyrrhitinate | 0.1 |
| Stevioside | 0.1 |
| Ethylalcohol | 3.0 |
| Flavor | 1.0 |
| Water | balance |
| Total : | 100.0 |

*$\overline{N}$ = 1.4
Degree of esterification = 1.05
Monoester content = 95%

EXAMPLE 11

Mouthwash

| Ingredient | % by weight |
| --- | --- |
| Ethylalcohol (90%) | 20.0 |
| Sodium saccharin | 0.3 |
| Lactitol coconut oil fatty acid monoester* | 0.3 |
| Lauryl diethanol amide | 0.3 |
| Flavor | 1.0 |
| Water | balance |
| Total : | 100.0 |

*Degree of esterification = 2.0

EXAMPLE 12

Mouthwash

| Ingredient | % by weight |
| --- | --- |
| Ethylalcohol (90%) | 20.0 |
| Sodium saccharin | 0.3 |
| Maltitol coconut oil fatty acid ester* | 0.3 |
| Lauryl diethanol amide | 0.3 |
| Flavor | 1.0 |
| Water | balance |
| Total : | 100.0 |

*$\overline{N}$ = 1.6
Degree of esterification = 2.0

The liquid dentifrices and mouthwashes of Examples 9-12 were prepared by dissolving the ingredients in water.

It was found that the oral compositions of Examples 3-12 are comparable to those of Examples 1 and 2 in feeling and stability.

What is claimed is:

1. An oral composition having a favorable feeling upon use and improved stability comprising: 0.1 to 5% by weight of the total composition of a fatty acid ester of a sugar alcohol selected from the group consisting of lactitol, maltitol, maltotriitol, maltotetraitol, maltopentaitol, maltohexaitol, maltoheptaitol and mixtures thereof, the acyl group of the sugar alcohol fatty acid ester having 8 to 20 carbon atoms and the balance being at least one other oral composition ingredient.

2. An oral composition according to claim 1, wherein the acyl group of said sugar alcohol fatty acid ester is selected from the group consisting of saturated acyl groups having 10 to 18 carbon atoms and unsaturated acyl groups having 16 to 18 carbon atoms.

3. An oral composition according to claim 2, wherein the acyl group of said sugar alcohol fatty acid ester is at least one acyl group selected from the group consisting of capryl, lauroyl, tridecanoyl, 2-methyllauroyl, myristoyl, pentadecanoyl, palmitoyl, stearoyl and isostearoyl.

4. An oral composition according to claim 1, wherein said sugar alcohol fatty acid ester is a lactitol fatty acid ester.

5. An oral composition according to claim 4, wherein said lactitol fatty acid ester has an average degree of esterification of 0.5-3.0.

6. An oral composition according to claim 5, wherein said lactitol fatty acid ester has a monoester content of at least 60% by weight.

7. An oral composition according to claim 1, wherein said sugar alcohol fatty acid ester is a fatty acid ester of a sugar alcohol selected from the group consisting of maltitol, maltotriitol, maltotetraitol, and mixtures thereof.

8. An oral composition according to claim 1, wherein said sugar alcohol contains at least 50% by weight of maltitol.

9. An oral composition according to claim 8, wherein the fatty acid ester of the sugar alcohol which contains at least 50% by weight of maltitol has an average degree of esterification of 0.5 to 3.0.

10. An oral composition according to claim 8, wherein the fatty acid ester of the sugar alcohol which contains at least 50% by weight of maltitol has a monoester content of at least 60% by weight.

11. An oral composition according to claim 1, in the form of a toothpaste, a toothpowder, a liquid dentrifrice or a mouthwash.

12. An oral composition according to claim 11, wherein said at least one other oral composition ingredient is selected from the group consisting of another surface-active agent, a polishing agent, a humectant, a binder, a sweetner, a flavoring agent, a fluorine compound, a bactericide, an inorganic phosphate, an organic phosphate, an enzyme, an antiinflammatory agent, sodium chloride and a solvent.

13. An oral composition according to claim 11, in the form of a toothpaste.

14. An oral composition according to claim 11, in the form of a toothpowder.

15. An oral composition according to claim 11, in the form of a liquid dentrifrice wherein said at least one other oral composition ingredient includes a solvent.

16. An oral composition according to claim 11, in the form of a mouthwash wherein said at least one other oral composition ingredient includes a solvent.

17. An oral composition according to claim 13, wherein said at least one other oral composition ingredient includes a polishing agent, a humectant, a binder, a sweetner, a flavor and a solvent.

18. An oral composition according to claim 14, wherein said at least one other oral composition ingredient includes a polishing agent, a humectant, a surfactant, a sweetner, a flavor and a solvent.

19. An oral composition according to claim 15, wherein said at least one other oral composition ingredient includes a humectant, a binder, a bactericide, a sweetner, a flavor and a solvent.

20. An oral composition according to claim 16, wherein said at least one other oral composition ingredient includes a solvent, a sweetner, a surfactant, and a flavor.

21. An oral composition according to claim 11, wherein said composition has a pH of 5.5 to 10.

22. An oral composition according to claim 21, wherein said composition has a pH of 6 to 8.5.

* * * * *